US00PP36502P2

(12) United States Plant Patent
Escriba

(10) Patent No.: US PP36,502 P2
(45) Date of Patent: Feb. 25, 2025

(54) **NEW GUINEA *IMPATIENS* PLANT NAMED 'Dongimaviosta'**

(50) Latin Name: *Impatiens hawkeri*
Varietal Denomination: Dongimaviosta

(71) Applicant: DUMMEN GROUP B.V., De Lier (NL)

(72) Inventor: Josep Escriba, Murcia (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 18/664,897

(22) Filed: May 15, 2024

(51) Int. Cl.
*A01H 5/02* (2018.01)
*A01H 6/16* (2018.01)

(52) U.S. Cl.
USPC ..... Plt./318.1
CPC ..... *A01H 6/165* (2018.05)

(58) Field of Classification Search
USPC ..... Plt./318.1
CPC ..... A01H 6/165; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Impatiens* plant named 'Dongimaviosta' characterized by its upright to outwardly spreading and mounding plant habit; moderately vigorous growth habit and moderately rapid growth rate; freely branching habit; dense and full appearance; dark green-colored leaves; freely and early flowering habit; flowers that are light purplish pink and bright purplish red bi-colored; and good garden performance.

1 Drawing Sheet

Botanical designation: *Impatiens hawkeri.*
Cultivar denomination: 'DONGIMAVIOSTA'.

CROSS REFERENCED TO CLOSELY-RELATED APPLICATION

An European Community Plant Breeder's Rights application for the instant plant was filed by the Applicant/Assignee, Dümmen Group B.V. of De Lier, The Netherlands on Sep. 22, 2023, application number 2023/1973 and published on Dec. 15, 2023. Foreign priority is claimed to this application.

STATEMENT REGARDING PRIOR DISCLOSURES BY INVENTOR & APPLICANT/ASSIGNEE

The Inventor and Applicant/Assignee assert that no sales, offers for sale or public distribution of the instant plant occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of New Guinea *Impatiens* plant, botanically known as *Impatiens hawkeri* and hereinafter referred to by the name 'Dongimaviosta'.

The new *Impatiens* plant is a product of a planned breeding program conducted by the Inventor in Koka, Ethiopia and Encinitas, California. The objective of the breeding program is to create new freely-branching, early and freely flowering New Guinea *Impatiens* plants with large attractive flowers and good garden performance.

The new *Impatiens* plant originated from a cross-pollination made by the Inventor in October, 2019 in Encinitas, California of a proprietary selection of *Impatiens hawkeri* identified as code number NN17-595500-006, not patented, as the female, or seed, parent with a proprietary selection of *Impatiens hawkeri* identified as code number NN17-527626-002, not patented, as the male, or pollen, parent. The new *Impatiens* plant was discovered and selected by the Inventor as a single flowering plant from within the progeny of the stated cross-pollination in a controlled greenhouse environment in Encinitas, California in June, 2020.

Asexual reproduction of the new *Impatiens* plant by terminal vegetative cuttings in a controlled greenhouse environment in Encinitas, California since July, 2020 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongimaviosta'. These characteristics in combination distinguish 'Dongimaviosta' as a new and distinct *Impatiens* plant:

1. Upright to outwardly spreading and mounding plant habit.

2. Moderately vigorous growth habit and moderately rapid growth rate.
3. Freely branching habit; dense and full appearance.
4. Dark green-colored leaves.
5. Freely and early flowering habit.
6. Flowers that are light purplish pink and bright purplish red bi-colored.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are larger than plants of the female parent selection.
2. Plants of the new *Impatiens* are not as freely flowering as plants of the female parent selection.
3. Flowers of plants of the new *Impatiens* are light purplish pink and bright purplish red bi-colored whereas flowers of plants of the female parent selection are dark pink in color.

Plants of the new *Impatiens* can be compared to plants of the male parent selection. Plants of the new *Impatiens* differ primarily from plants of the male parent selection in the following characteristics:

1. Plants of the new *Impatiens* are more compact than plants of the male parent selection.
2. Plants of the new *Impatiens* have larger flowers than plants of the male parent selection.
3. Flowers of plants of the new *Impatiens* are light purplish pink and bright purplish red bi-colored whereas flowers of plants of the male parent selection are pinkish purple in color.

Plants of the new *Impatiens* can be compared to plants of *Impatiens hawkeri* 'Dongipetorsta 21', disclosed in U.S. Plant Pat. No. 34,427. In side-by-side comparisons, plants of the new *Impatiens* differ primarily from plants of 'Dongipetorsta 21' in the following characteristics:

1. Plants of the new *Impatiens* are smaller than plants of 'Dongipetorsta 21'.
2. Plants of the new *Impatiens* flower earlier than plants of 'Dongipetorsta 21'.
3. Plants of the new *Impatiens* have larger flowers than plants of 'Dongipetorsta 21'.
4. Flowers of plants of the new *Impatiens* are light purplish pink and bright purplish red bi-colored whereas flowers of plants of 'Dongipetorsta 21' are orangish red and pale purple pink bi-colored.

BRIEF DESCRIPTION OF THE PHOTOGRAPH

The accompanying colored photograph illustrates the overall appearance of the new *Impatiens* plant showing the colors as true as it is reasonably possible to obtain in colored reproductions of this type. Colors in the photograph may differ slightly from the color values cited in the detailed botanical description which accurately describe the colors of the new *Impatiens* plant. The photograph is a side perspective view of a typical flowering plant of 'Dongimaviosta' grown in a container.

DETAILED BOTANICAL DESCRIPTION

The aforementioned photograph and following observations, measurements and values describe plants grown during the summer in 17-cm containers in a polyethylene-covered greenhouse in Puerto Lumbreras, Murcia, Spain and under cultural practices typical of commercial New Guinea *Impatiens* production. During the production of the plants, day temperatures averaged 30° C., night temperatures averaged 22° C. and light levels averaged 650/m$^2$/hour. Plants were three months old when the photograph was taken and five months old when the description was taken. In the following description, color references are made to The Royal Horticultural Society Colour Chart, Second Edition, except where general terms of ordinary dictionary significance are used.

Botanical classification: *Impatiens hawkeri* 'Dongimaviosta'.

Parentage:

*Female, or seed, parent.*—Proprietary selection of *Impatiens hawkeri* identified as code number NN17-595500-006, not patented.

*Male, or pollen, parent.*—Proprietary selection of *Impatiens hawkeri* identified as code number NN17-527626-002, not patented.

Propagation:

*Type.*—By terminal vegetative cuttings.

*Time to initiate roots, summer.*—About 14 days at temperatures about 20° C.

*Time to initiate roots, winter.*—About 17 days at temperatures about 20° C.

*Time to produce a rooted young plant, summer.*—About 20 days at temperatures about 20° C.

*Time to produce a rooted young plant, winter.*—About 30 days at temperatures about 20° C.

*Root description.*—Medium in thickness, fibrous; typically white in color, actual color of the roots is dependent on substrate composition, water quality, fertilizers, substrate temperature and age of roots.

*Rooting habit.*—Moderately freely branching; medium density.

Plant description:

*Plant and growth habit.*—Upright to outwardly spreading and mounding plant habit; broad inverted triangle in overall shape; freely branching habit with lateral branches potentially developing at every node; dense and full appearance; moderately vigorous growth habit and moderate growth rate.

*Plant height.*—About 15.5 cm.

*Plant diameter.*—About 24 cm.

Lateral branch description:

*Length.*—About 12 cm.

*Diameter.*—About 7 mm.

*Internode length.*—About 3.5 cm.

*Strength.*—Moderately strong; flexible.

*Aspect.*—Initially upright to outwardly spreading.

*Texture and luster.*—Smooth, glabrous; semi-glossy.

*Color, developing.*—Close to 183A.

*Color, developed.*—Close to 183A.

Leaf description:

*Arrangement.*—Typically alternate or in whorls; simple.

*Length.*—About 9 cm.

*Width.*—About 4.4 cm.

*Shape.*—Ovate.

*Apex.*—Apiculate.

*Base.*—Obtuse.

*Margin.*—Serrate with ciliation.

*Texture and luster, upper and lower surfaces.*—Smooth, glabrous; leathery; semi-glossy.

*Venation pattern.*—Pinnate; arcuate.

*Color*.—Developing and fully expanded leaves, upper surface: Close to 147A; venation, close to 183A to 183B. Developing and fully expanded leaves, lower surface: Close to 183A; venation, close to 183C.

*Petiole length*.—About 1.3 cm.

*Petiole diameter*.—About 3 mm.

*Petiole texture and luster, upper and lower surfaces*.—Smooth, glabrous; semi-glossy.

*Petiole color, upper and lower surfaces*.—Close to 183C.

Flower description:

*Flower type and flowering habit*.—Single-type, rounded axillary flowers; freely flowering habit, typically about five to six flower buds and open flowers per lateral branch and about 80 flowers developing per plant during the flowering season; flowers positioned above and beyond the foliar plane, flowers typically face upright to outwardly.

*Flower longevity*.—Flowers typically last about four to seven days on the plant under greenhouse conditions; petals self-cleaning, gynoecium persistent.

*Fragrance*.—None detected.

*Natural flowering season*.—Year-round under greenhouse conditions; in the garden, flowering from spring until fall in Spain; early flowering habit, plants typically begin flowering about eight weeks after planting.

*Flower buds*.—Length: About 1 cm. Diameter: About 1 cm. Shape: Ovoid. Texture and luster: Smooth, glabrous; slightly glossy. Color: Close to 61C.

*Flower diameter*.—About 7 cm by 7 cm.

*Flower depth*.—About 3.5 cm.

*Petals*.—Quantity and arrangement: Five per flower in a single whorl. Length: About 3.25 cm. Width: About 3.2 cm. Shape: Obcordate. Apex: Emarginate. Base: Cuneate. Margin: Entire; not undulate. Texture and luster, upper and lower surfaces: Smooth, glabrous; slightly glossy; iridescent. Color: When opening and fully opened, upper surface: Ground color, close to 62D; secondary color, close to 67A; venation, similar to lamina colors; colors do not change with subsequent development. When opening and fully opened, lower surface: Close to 67A; venation, close to 67A; color does not change with subsequent development.

*Sepals*.—Quantity and arrangement: Three in a single whorl; one modified into an elongated spur. Length: About 1.8 cm. Width: About 7 mm. Shape: Ovate. Apex: Acuminate. Base: Obtuse. Margin: Entire. Sepal texture and luster, upper and lower surfaces: Smooth, glabrous; slightly glossy. Color, upper and lower surfaces: Close to 60A. Spur length: About 4 cm. Spur diameter: About 1 mm. Spur shape: Acicular. Spur texture and luster: Smooth, glabrous; semi-glossy. Spur color: Close to 150D.

*Peduncles*.—Length: About 6 cm. Diameter: About 3 mm. Angle: About 45° from stem axis. Strength: Moderately strong; flexible. Texture and luster: Smooth, glabrous; semi-glossy. Color: Close to 149D.

*Reproductive organs*.—Stamens: Quantity: Five fused at anthers; filaments free. Anther size: About 1 mm by 5 mm. Anther shape: Oblong. Anther color: Close to 155B. Pollen amount: Abundant. Pollen color: Close to 160D. Pistils: Quantity per flower: One. Pistil length: About 5 mm. Stigma diameter: About 1 mm. Stigma shape: Crested. Stigma color: Close to 145D. Style length: About 4 mm. Style color: Close to 145A. Ovary color: Close to 144A.

*Seeds and fruits*.—To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 45° C.

It is claimed:

1. A new and distinct *Impatiens* plant named 'Dongimaviosta' as illustrated and described herein.

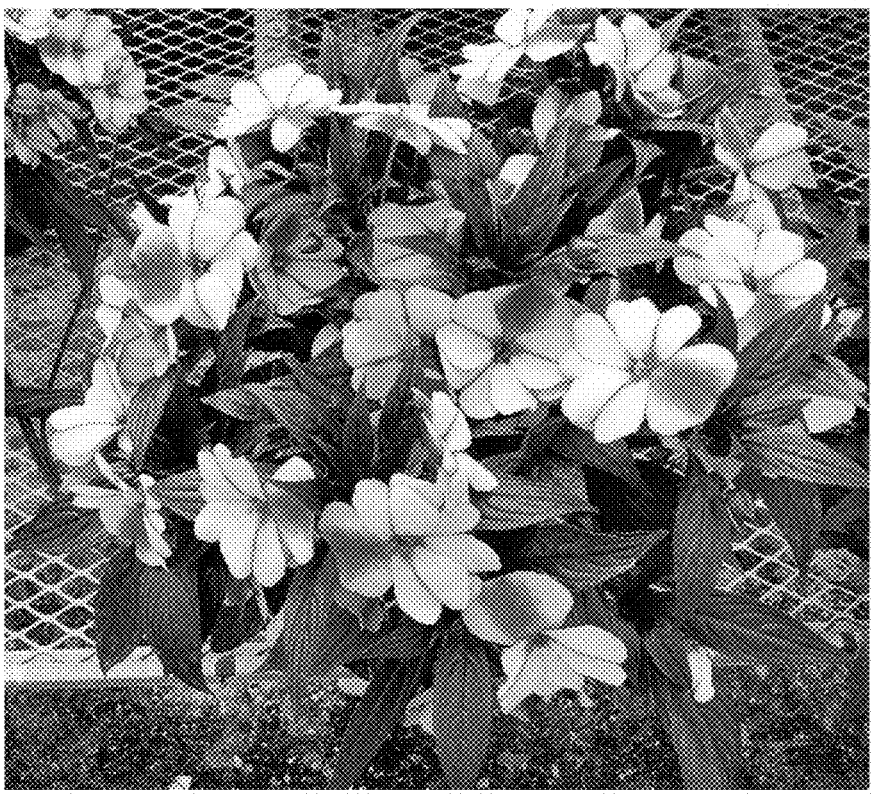

* * * * *